(12) United States Patent
Li

(10) Patent No.: US 11,311,375 B2
(45) Date of Patent: Apr. 26, 2022

(54) STENTS WITH ANCHORING SECTIONS

(71) Applicant: St. Jude Medical, Cardiology Division, Inc., St. Paul, MN (US)

(72) Inventor: Xue Mei Li, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 249 days.

(21) Appl. No.: 16/591,694

(22) Filed: Oct. 3, 2019

(65) Prior Publication Data
US 2020/0030091 A1 Jan. 30, 2020

Related U.S. Application Data

(62) Division of application No. 15/312,005, filed as application No. PCT/US2015/031691 on May 20, 2015, now Pat. No. 10,500,042.

(60) Provisional application No. 62/001,793, filed on May 22, 2014.

(51) Int. Cl.
*A61F 2/24* (2006.01)

(52) U.S. Cl.
CPC .......... *A61F 2/2418* (2013.01); *A61F 2/2409* (2013.01); *A61F 2/2436* (2013.01); *A61F 2220/0008* (2013.01); *A61F 2230/008* (2013.01); *A61F 2230/0034* (2013.01); *A61F 2230/0067* (2013.01); *A61F 2250/0069* (2013.01)

(58) Field of Classification Search
USPC .................................................. 623/1.1–3.1
See application file for complete search history.

(56) References Cited

U.S. PATENT DOCUMENTS

| | | |
|---|---|---|
| 3,657,744 A | 4/1972 | Ersek |
| 4,275,469 A | 6/1981 | Gabbay |
| 4,491,986 A | 1/1985 | Gabbay |

(Continued)

FOREIGN PATENT DOCUMENTS

| | | |
|---|---|---|
| DE | 10121210 A1 | 11/2002 |
| DE | 19857887 B4 | 5/2005 |

(Continued)

OTHER PUBLICATIONS

International Search Report for Application No. PCT/US2015/031691 dated Aug. 14, 2015.

(Continued)

*Primary Examiner* — Yashita Sharma
(74) *Attorney, Agent, or Firm* — Lerner, David, Littenberg, Krumholz & Mentlik, LLP

(57) ABSTRACT

A stent (300, 400, 400') for a prosthetic heart valve includes a body having an inflow end (310, 410) and an outflow end (312, 412), and an anchoring section (340, 440) adjacent the inflow end. The anchoring section may include structure (342, 344, 420) that extends radially outwardly from the body when the stent is in an expanded condition. The stent may include a transition section (370, 470) between the body and the anchoring section, the transition section in the expanded condition of the stent having a diameter that is smaller than the diameters of the body and the anchoring section. When implanted into a native valve annulus, such as the mitral valve annulus, the anchoring section may help the stent resist migrating away from the native valve annulus.

13 Claims, 6 Drawing Sheets

(56) References Cited

U.S. PATENT DOCUMENTS

| | | |
|---|---|---|
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 8,840,663 B2 | 9/2014 | Salahieh et al. |
| 9,636,222 B2 | 5/2017 | Oslund |
| 9,687,342 B2 | 6/2017 | Figulla et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0198315 A1 | 8/2009 | Boudjemline |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2012/0303116 A1 | 11/2012 | Gorman, III et al. |

(56) References Cited

U.S. PATENT DOCUMENTS

| | | | | |
|---|---|---|---|---|
| 2014/0214157 | A1* | 7/2014 | Bortlein | A61F 2/2427 623/2.11 |
| 2015/0196390 | A1 | 7/2015 | Ma et al. | |

FOREIGN PATENT DOCUMENTS

| | | |
|---|---|---|
| DE | 10121210 A1 | 11/2005 |
| DE | 10121210 B4 | 11/2005 |
| DE | 102005003632 A1 | 8/2006 |
| DE | 102005052628 A1 | 5/2007 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1849440 A1 | 10/2007 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 01056500 A2 | 8/2001 |
| WO | 2001054625 A1 | 8/2001 |
| WO | 2001076510 A2 | 10/2001 |
| WO | 2002036048 A1 | 5/2002 |
| WO | 0247575 A2 | 6/2002 |
| WO | 02067782 A2 | 9/2002 |
| WO | 2003047468 A1 | 6/2003 |
| WO | 2005070343 A1 | 8/2005 |
| WO | 06073626 A2 | 7/2006 |
| WO | 2007053243 A2 | 5/2007 |
| WO | 2007071436 A2 | 6/2007 |
| WO | 08070797 A2 | 6/2008 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012095116 A1 | 7/2012 |
| WO | 2013037519 A1 | 3/2013 |

OTHER PUBLICATIONS

Ruiz, Carlos, Overview of PRE-CE Mark Transcatheter Aortic Valve Technologies, Euro PCR, dated May 25, 2010.

Percutaneous aortic valve replacement: resection before implantation, 836-840, Quaden, Rene et al., European J. of Cardio-thoracic Surgery, 27 (2005).

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H.R., et al., European Heart Journal (1992) 13, 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Feb. 6, 2006).

"Minimally invasive cardiac surgery", M. J. Mack, Surgical Endoscopy, 2006, 20:S488-S492, DOI: 10.1007/s00464-006-0110-8 (presented Apr. 24, 2006).

"Transapical Transcatheter Aortic Valve Implantation in Humans", Samuel V. Lichtenstein et al., Circulation. 2006; 114: 591-596 (Jul. 31, 2006).

"Closed heart surgery: Back to the future", Samuel V. Lichtenstein, The Journal of Thoracic and Cardiovascular Surgery, vol. 131, No. 5, pp. 941-943.

"Transapical approach for sutureless stent-fixed aortic valve implantation: experimental results"; Th. Walther et al., European Journal of Cardio-thoracic Surgery 29 (2006) 703-708 (Jan. 30, 2006).

"Transapical aortic valve implantation: an animal feasibility study"; Todd M. Dewey et al., The annals of thoracic surgery 2006; 82: 110-6 (Feb. 13, 2006).

Textbook "Transcatheter Valve Repair", 2006, pp. 165-186.

* cited by examiner

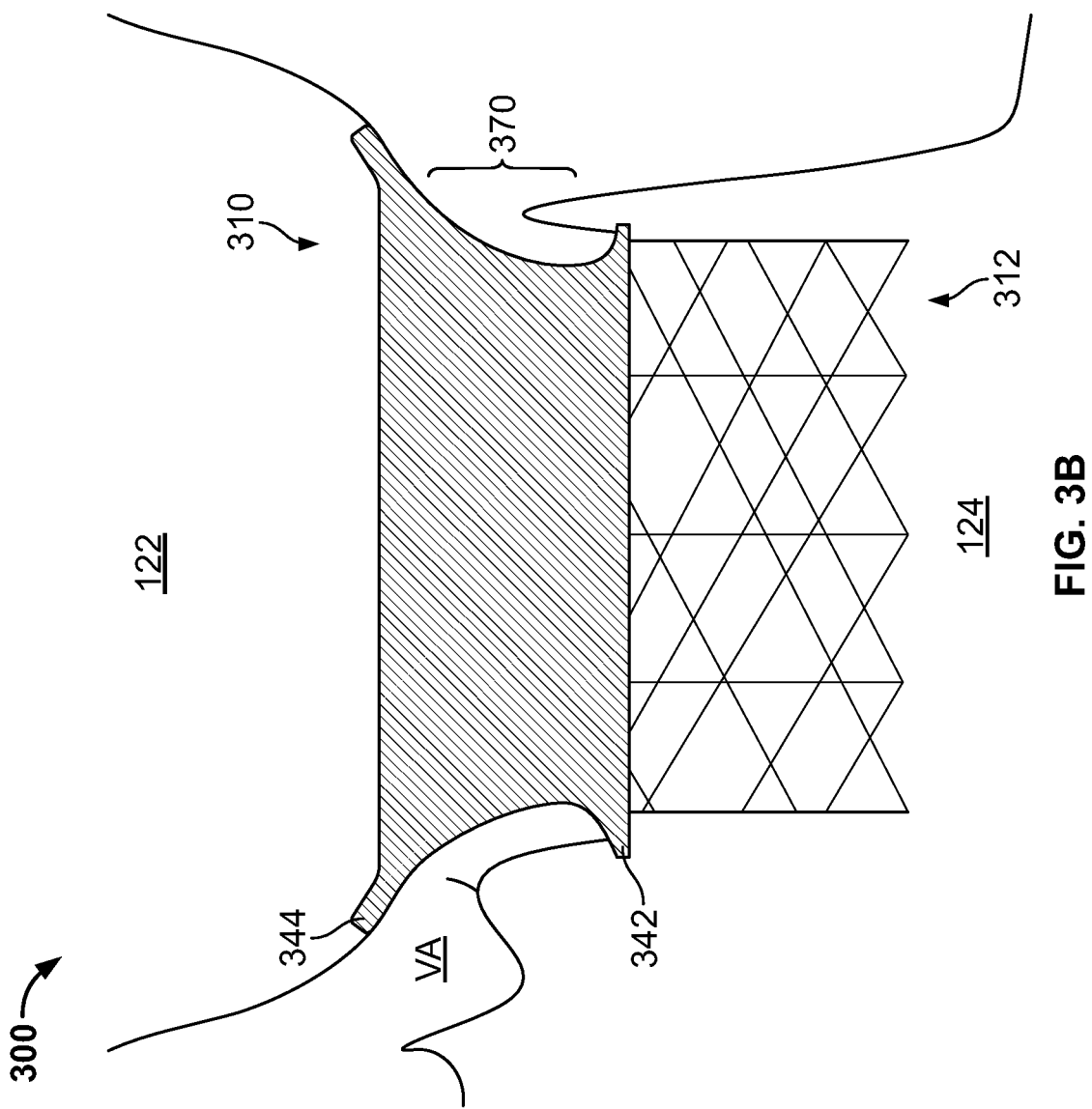

STENTS WITH ANCHORING SECTIONS

CROSS-REFERENCE TO RELATED APPLICATIONS

This application is a divisional of U.S. patent application Ser. No. 15/312,005 filed Nov. 17, 2016, which is a national phase entry under 35 U.S.C. § 371 of International Application No. PCT/US2015/031691, filed May 20, 2015, which claims the benefit of the filing date of U.S. Provisional Application No. 62/001,793, filed May 22, 2014, entitled "STENT WITH ANCHORING SECTIONS," the disclosures of which are all hereby incorporated by reference herein.

BACKGROUND

The present disclosure relates to heart valve replacement and, in particular, to collapsible prosthetic heart valves. More particularly, the present disclosure relates to prosthetic heart valves that facilitate secure positioning within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open chest, open heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve is generally first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon expandable valves, this generally involves releasing the entire valve, assuring its proper location, and then expanding a balloon positioned within the valve stent. For self-expanding valves, on the other hand, the stent automatically expands as the sheath covering the valve is withdrawn.

BRIEF SUMMARY

According to one embodiment of the disclosure, a stent includes an inflow end, an outflow end, a body section extending from the outflow end toward the inflow end, and an anchoring section adjacent the inflow end having a first annular disc and a second annular disc. The stent may have a collapsed condition and an expanded condition. The first annular disc and the second annular disc may each extend radially outwardly from the body section when the stent is in the expanded condition.

According to another embodiment of the disclosure, a stent includes an inflow end, an outflow end, a body section extending from the outflow end toward the inflow end, an anchoring section adjacent the inflow end; and a transition section between the body section and the anchoring section. The transition section may have a diameter that is smaller than diameters of the body section and the anchoring section. The stent may have a collapsed condition, an expanded condition, and a longitudinal axis. The anchoring section may extend radially outwardly from the longitudinal axis when the stent is in the expanded condition.

BRIEF DESCRIPTION OF THE DRAWINGS

Various embodiments of the present disclosure are described herein with reference to the drawings, wherein:

FIG. 3B is a schematic representation of the stent of FIG. 3A disposed in a native valve annulus;

Various embodiments of the present disclosure will now be described with reference to the appended drawings. It is to be appreciated that these drawings depict only some embodiments of the disclosure and are therefore not to be considered limiting of its scope.

DETAILED DESCRIPTION

Blood flows through the mitral valve from the left atrium to the left ventricle. As used herein, the term "inflow end," when used in connection with a prosthetic atrioventricular heart valve, refers to the end of the heart valve closest to the atrium when the heart valve is implanted in a patient, whereas the term "outflow end," when used in connection with a prosthetic atrioventricular heart valve, refers to the end of the heart valve closest to the ventricle when the heart valve is implanted in a patient. Further, when used herein with reference to a delivery device, the terms "proximal" and "distal" are to be taken as relative to a user using the device in an intended manner. "Proximal" is to be understood as relatively close to the user and "distal" is to be understood as relatively farther away from the user. Also, as used herein, the terms "substantially," "generally," and "about" are intended to mean that slight deviations from absolute are included within the scope of the term so modified. Generally, materials described as being suitable for components in one embodiment may also be suitable for similar components described in other embodiments. Although embodiments disclosed herein are generally described in relation to replacement of a native mitral valve, it should be understood that the disclosed embodiments and variants thereof may be suitable to replace other valves, including other heart valves such as the aortic or tricuspid valve. When ranges of values are described herein, those ranges are intended to include sub-ranges. For example, a recited range of 1 to 10 includes 2, 5, 7, and other single values, as well as ranges of 2 to 6, 3 to 9, 4 to 5, and others.

Figure 1:
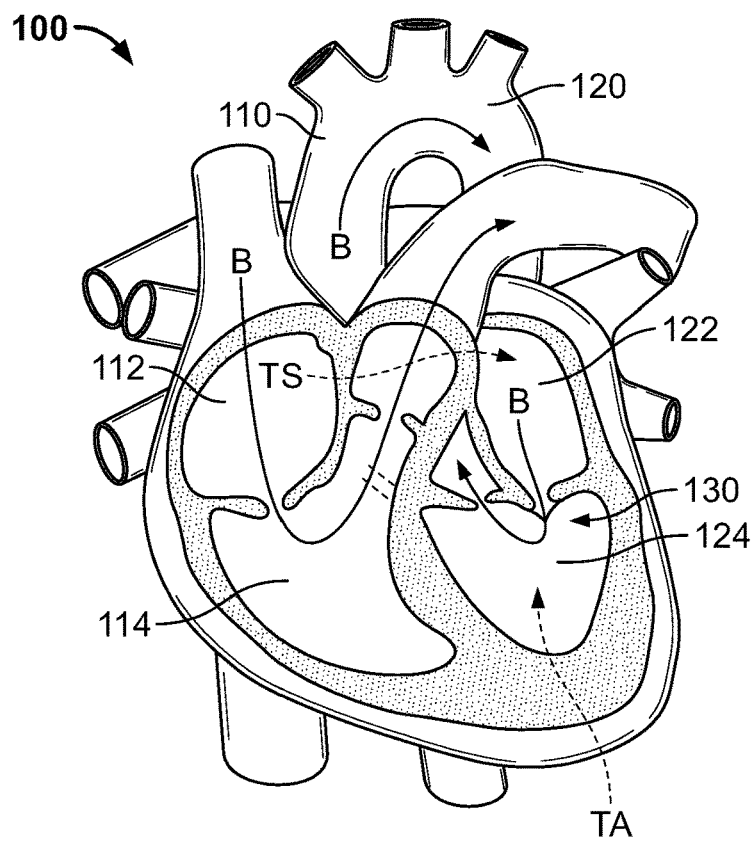
FIG. 1 is a schematic cutaway representation of a human heart showing a transapical delivery approach.

FIG. 1 is a schematic cutaway representation of human heart 100. The human heart includes two atria and two ventricles: right atrium 112 and left atrium 122, and right ventricle 114 and left ventricle 124. Heart 100 further includes aorta 110, and aortic arch 120. Disposed between the left atrium and the left ventricle is mitral valve 130. Mitral valve 130, also known as the bicuspid valve or left atrioventricular valve, is a dual-flap that opens as a result of increased pressure in left atrium 122 as it fills with blood. As atrial pressure increases above that of left ventricle 124, mitral valve 130 opens and blood passes into left ventricle 124. Blood flows through heart 100 in the direction shown by arrows "B".

A dashed arrow, labeled "TA", indicates a transapical approach of implanting a prosthetic heart valve, in this case to replace the mitral valve. In transapical delivery, a small incision is made between the ribs and into the apex of left ventricle 124 to deliver the prosthetic heart valve to the target site. A second dashed arrow, labeled "TS", indicates a transseptal approach of implanting a prosthetic heart valve in which the valve is passed through the septum between right atrium 112 and left atrium 122. Other approaches for implanting a prosthetic heart valve are also possible and may be used in connection with the disclosed embodiments.

Figure 2:
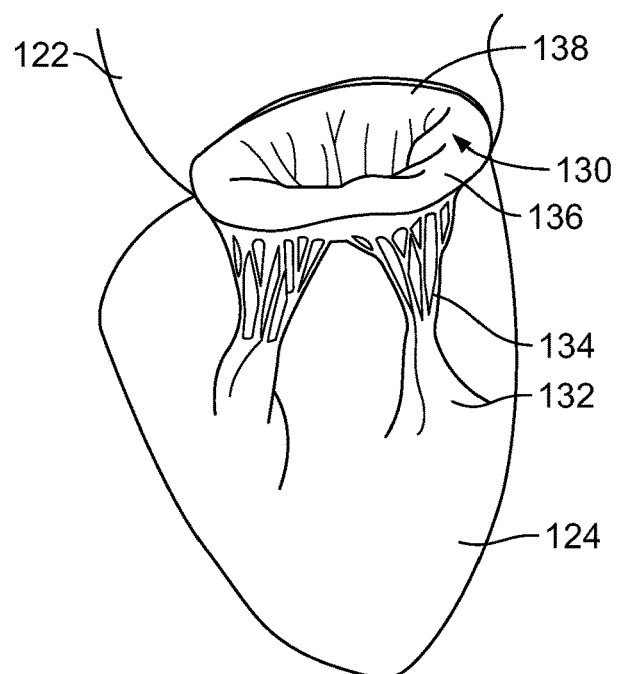
FIG. 2 is a schematic representation of a native mitral valve and associated cardiac structures.

FIG. 2 is a more detailed schematic representation of native mitral valve 130 and its associated structures. As previously noted, mitral valve 130 includes two flaps or leaflets, posterior leaflet 136 and anterior leaflet 138, disposed between left atrium 122 and left ventricle 124. Cord-like tendons, known as chordae tendineae 134, connect the two leaflets 136, 138 to the medial and lateral papillary muscles 132. During atrial systole, blood flows from higher pressure in left atrium 122 to lower pressure in left ventricle 124. When left ventricle 124 contracts in ventricular systole, the increased blood pressure in the chamber pushes leaflets 136, 138 to close, preventing the backflow of blood into left atrium 122. Since the blood pressure in left atrium 122 is much lower at this point in a heartbeat than that in left ventricle 124, leaflets 136, 138 attempt to evert to the low pressure regions. Chordae tendineae 134 prevent the eversion by becoming tense, thus pulling on leaflets 136, 138 and holding them in the closed position.

When a self-expanding prosthetic heart valve is implanted in a patient, for example at the annulus of a native heart valve, it generally is biased towards an expanded condition, providing radial force to anchor the valve in place. This may be true of prosthetic heart valves used to replace the aortic valve as well as those used to replace the mitral valve. When replacing the aortic valve, the radial force may anchor the prosthetic valve onto calcified native leaflets around the aortic root. When replacing the left atrioventricular valve (known as the mitral or bicuspid valve) or the right atrioventricular valve (known as the tricuspid valve), anchoring with radial force may be more challenging. This may be at least in part due to the fact that there is relatively little tissue in the left atrium adjacent the mitral valve to which a stent may anchor via radial force. This is also true of the area available in the right atrium adjacent the tricuspid valve. In contrast, there is a relatively large amount of solid tissue in the aorta adjacent the aortic valve available for anchoring a stent via radial force. For example, the aortic root, which is adjacent the aortic valve, may provide ample structure for anchoring a stent via radial force. In addition, if the radial force used to anchor a prosthetic heart valve is too high, damage may occur to heart tissue. If, instead, the radial force is too low, the heart valve may move from its implanted position. For example, a prosthetic mitral valve may migrate into left ventricle 124 or left atrium 122 if the radial force is too low, requiring emergency surgery to remove the displaced valve. The potential for such movement may be heightened in mitral valve applications, particularly if a low profile valve is used.

Another potential issue with prosthetic heart valves is inadequate sealing between the prosthetic valve and the native tissue. For example, if a prosthetic heart valve is implanted at the annulus of mitral valve 130 in a patient, improper or inadequate sealing may result in blood flowing from left ventricle 124 into left atrium 122, even if the prosthetic leaflets of the valve assembly are working properly. This may occur, for example, if blood flows in a retrograde fashion between the outer perimeter of the prosthetic heart valve and the native tissue at the site of implantation. This phenomenon is known as perivalvular (or paravalvular) leak ("PV leak").

Figure 3A:
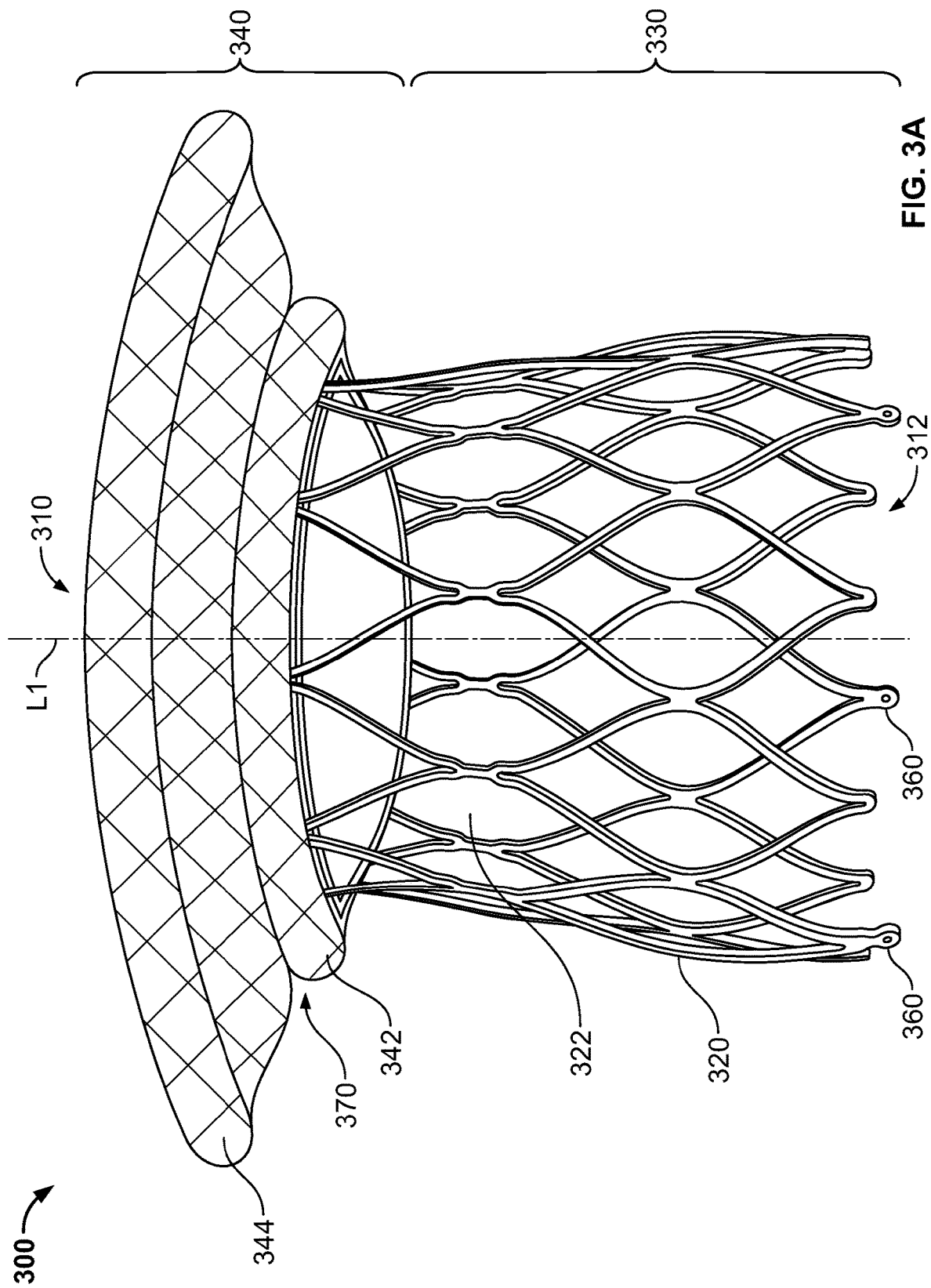
FIG. 3A is a bottom perspective view of a stent of a prosthetic heart valve according to an embodiment of the disclosure.

FIG. 3A illustrates a stent 300 of a prosthetic heart valve according to one embodiment of the disclosure. Stent 300 may be collapsible and expandable for use in a prosthetic heart valve intended to replace the function of a native heart valve of a patient, such as the mitral valve (see native mitral valve 130 of FIGS. 1-2). In FIG. 3A, stent 300 is illustrated in an expanded condition. The remaining components that would be attached to stent 300 to form a prosthetic heart valve, such as prosthetic valve leaflets and a cuff, are omitted from the figure for clarity.

Stent 300 may be formed from biocompatible materials that are capable of self-expansion, such as, for example, shape memory alloys including Nitinol. Generally, stent 300 extends from inflow end 310 to outflow end 312. A plurality of struts 320 may form cells 322 in stent 300, the cells being connected to one another in one or more annular rows around the stent. Cells 322 may all be of substantially the same size around the perimeter and along the length of stent 300. However, cells 322 nearer inflow end 310 may be larger or smaller than the cells nearer outflow end 312.

Stent 300 may have a body or leaflet section 330 extending from outflow end 312 toward inflow end 310. Leaflet section 330 may have a substantially cylindrical shape. When used in a prosthetic heart valve, prosthetic valve leaflets may be attached directly or indirectly to an inner surface of leaflet section 330. Leaflet section 330 may take other shapes, such as a substantially conical shape or a general "D"-shape, which may better correspond to the shape of the native valve annulus in which stent 300 is implanted.

As noted above, stent 300 may be provided with prosthetic valve leaflets. One, two, or more prosthetic valve leaflets may be included in a valve assembly attached to stent 300. The valve assembly may be substantially cylindrical, although other shapes may be suitable, and may include a cuff attached to leaflet section 330. The prosthetic leaflets may be attached to the cuff or directly to struts 320 of leaflet section 330. When used to replace a mitral valve, the prosthetic leaflets replace the function of native mitral valve leaflets 136 and 138 described above in connection with FIG. 2. That is, the prosthetic leaflets coapt with one another to function as a one-way valve. It should be appreciated that a prosthetic heart valve incorporating stent 300 may have more than two prosthetic leaflets when used to replace the mitral valve or other cardiac valves within a patient. Both the cuff and leaflets may be wholly or partly formed of any suitable biological material, such as bovine or porcine pericardium, or polymers, such as polytetrafluoroethylene (PTFE), urethanes and the like. The valve assembly may be secured to stent 300 by suturing to struts 320 or by using tissue glue, ultrasonic welding or other suitable methods.

An anchoring or clamp section 340 may be positioned adjacent the leaflet section 330 and inflow end 310. Clamp section 340 may include a first disc 342 and a second disc 344. Each disc 342, 344 may be generally annular and may take the form of a mesh or braid, including metal braids such as braided Nitinol. Alternatively, first disc 342 and/or second disc 344 may be formed of fabrics and/or polymers, such as PTFE, urethanes, and the like. In still other embodiments, discs 342 and 344 may be formed of tissue, such as bovine or porcine cardiac tissue. Some or all of the above materials may be used in combination with a coating, such as a collagen coating, a fibrin coating, or a polymer coating (such as a silicone coating). In addition, while discs 342 and 344 may each be formed of the same material, disc 342 may be formed of any one of the materials described above while disc 344 may be formed of a different material described above. Disc 342 may be attached to inflow end 310 by, for example, sutures, metal pressed clamping, adhesives, ultrasonic welding, or other suitable methods. Disc 344 may be attached to disc 342 by any suitable method. Alternatively, discs 342 and 344 may be formed as a single unit from the same material. When discs 342 and 344 are both formed of the same material as stent 300, discs 342 and 344 may be formed as a single unit with the remainder of stent 300. Preferably, clamp section 340 is positioned in series with leaflet section 330. In other words, neither disc 342 nor disc 344 overlap struts 320 of stent 300 when the stent is in the collapsed condition. When in the expanded condition, there is no overlap or minimal overlap between the discs 342, 344 and the struts 320. As described in more detail below, this may help reduce the profile of stent 300 during delivery.

First disc 342 may be positioned closer to outflow end 312 than second disc 344, which may be positioned farther away from outflow end 312. The diameter of first disc 342 may be smaller than the diameter of second disc 344. In other words, second disc 344 may extend farther radially outwardly from a longitudinal axis L1 of stent 300. With this configuration, stent 300 may be implanted in a native mitral valve annulus VA with first disc 342 positioned within left ventricle 124 and second disc 344 positioned within left atrium 122, as illustrated in FIG. 3B.

When positioned in the native mitral valve annulus VA, second disc 344 on the atrial side of native valve annulus VA helps anchor stent 300 in place, resisting migration into left ventricle 124. Similarly, first disc 342 on the ventricular side of native valve annulus VA helps resist migration of stent 300 into left atrium 122. The relatively large size of second disc 344 compared to first disc 342 may be useful in that there may be a greater anatomical area available for contact on the atrial side of native valve annulus VA. As a result, stent 300 may rely less on radial anchoring force and thus avoid some or all of the potential issues described above in connection with the use of radial force to anchor a prosthetic heart valve within a native valve annulus. If formed of a material that may be shape-set, first disc 342 may be shape-set, for example by heat setting, such that it flares or is biased away from outflow end 312. Similarly, second disc 344 may be shape-set such that it flares or is biased toward outflow end 312. In this configuration, first disc 342 and second disc 344 may act together to pinch native valve annulus VA. Such biasing, however, is not required. Thus, in other embodiments, one or both of first disc 342 and second disc 344 may extend at an angle of about 90 degrees from the longitudinal axis $L1L_1$ of stent 300 when stent 300 is in the relaxed or expanded condition. It should be understood that other angles or ranges of angles from longitudinal axis L1, for example between about 60 degrees and about 120 degrees, between about 70 degrees and about 110 degrees, or between about 80 degrees and about 100 degrees, may also be suitable.

The use of a mesh or braided wire to form first disc 342 and second disc 344 may provide a relatively large surface area with which the native anatomy may interact and into which tissue can grow, helping secure stent 300 further. This may result in both better anchoring and better sealing of the prosthetic heart valve incorporating stent 300. Additionally, sealing may be further improved by providing a fabric or other covering over first disc 342 and second disc 344, which may enhance tissue ingrowth and healing. In certain arrangements, such fabric or other covering may be applied only to first disc 342 or only to second disc 344.

As illustrated in FIG. 3B, first disc 342 and second disc 344 may be part of a single continuous mesh or braided structure, with the discs being at substantially opposite ends of the braided structure. However, each disc may be provided independently of the other. Whether separate structures or part of one continuous structure, a space between first disc 342 and second disc 344 defines an annulus gap 370 in which the native valve annulus VA is positioned when stent 300 is implanted. Having the first disc 342 and the second disc 344 on opposite ends of an annulus gap helps anchor stent 300 in the native valve annulus VA, and further may help restrict movement of native valve leaflets that may still be partially or fully intact.

When being used in a prosthetic heart valve for replacing the native mitral valve of a patient, stent 300 is crimped to a collapsed condition and positioned within a catheter or similar structure of a delivery device. The delivery device may, for example, be inserted through the apex of the heart (transapical delivery) or through the femoral artery and passed through the vasculature to the implant site (transfemoral delivery), although other delivery routes may be used. If a transapical method is used, retaining tabs 360 on outflow end 312 of stent 300 may be connected to the delivery device and may be configured to maintain a connection between stent 300 and the delivery device prior to full release of the stent. When stent 300 is crimped and in the collapsed condition, clamp section 340 extends away from leaflet section 330. Once the delivery device is near the site of implantation, the sheath or other member compressing stent 300 may be slowly retracted to reveal stent 300 and allow it to expand to the expanded condition. As the sheath is retracted, clamp section 340 may begin to expand prior to leaflet section 330, such that the proper positioning of first disc 342 and second disc 344 relative to the native valve annulus VA may be confirmed before continuing release of the stent. Once confirmed, retraction of the sheath may be continued to allow leaflet section 330, along with the valve assembly with prosthetic leaflets positioned therein, to expand into the implantation site. If the positioning is acceptable to the user, the sheath may be further retracted to release retaining tabs 360 to fully release stent 300 into the patient. If the positioning is not acceptable, the sheath may be advanced in the opposite direction to partially or completely resheathe stent 300. Once partially or fully resheathed, the user may attempt to properly position and release stent 300 again. Similarly, when using other delivery routes, such as a transseptal route, retaining tabs may be formed near inflow end 310 with the outflow end 312 being expanded first. Further, as shown in FIG. 3B, the valve 300 may be implanted such that leaflet section 330 is substantially or fully in a supraannular position. When used in the context of an atrioventricular valve, supraannular refers to a position closer to a position beyond the native valve annulus in the direction of the ventricle.

When implanting a collapsible prosthetic heart valve, the size of the prosthetic heart valve in the collapsed condition, including stent 300, may be an important factor. For example, a prosthetic heart valve that retains a large profile in the collapsed condition will need to be delivered using a delivery device with a correspondingly large catheter. On the other hand, a prosthetic heart valve with a small profile in the collapsed condition may be implanted using a delivery device with a correspondingly small catheter. If first disc 342 and/or second disc 344 were positioned along a portion of leaflet section 330, stent 300 would have a relatively large crimp profile and require a relatively large catheter. In the illustrated embodiment, clamp section 340 and leaflet section 330 are positioned in series such that, when crimped and loaded into a delivery device in the collapsed condition, most or all of first disc 342 and second disc 342 do not overlap with struts 320 of leaflet section 330. Avoiding this overlap facilitates a reduction in crimp profile, thus allowing relatively small catheters to be used to deliver and implant prosthetic heart valves incorporating stent 300.

Figure 4A:
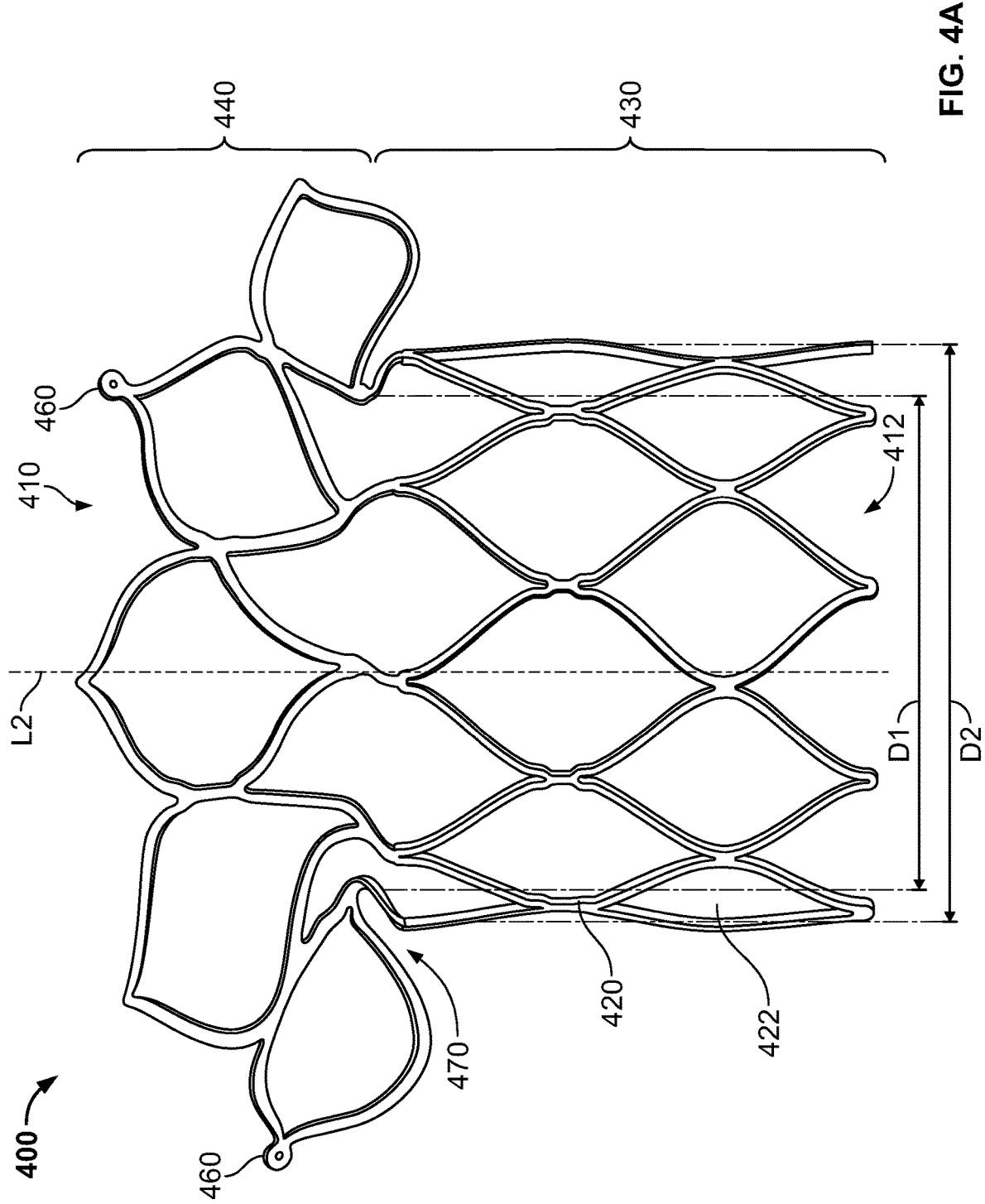
FIG. 4A is a front view of a front portion of a stent of a prosthetic heart valve according to another embodiment of the disclosure.

FIG. 4A illustrates a stent 400 of a prosthetic heart valve according to another embodiment of the disclosure. Stent 400 may have features similar to stent 300. For example, stent 400 may be collapsible and expandable for use in a prosthetic heart valve intended to replace the function of a native heart valve of a patient. Stent 400 is illustrated in FIG. 4A in an expanded condition, omitting the back side of the stent for clarity, and omitting other components that could be attached to the stent to form a prosthetic heart valve, such as prosthetic valve leaflets and a cuff.

Stent 400 may be formed from biocompatible materials that are capable of self-expansion, including Nitinol or super-elastic polymeric materials. An inflow end 410 may be positioned on the opposite end of stent 400 than an outflow end 412. A plurality of struts 420 may form cells 422 connected to one another in one or more annular rows around the stent. As with stent 300, cells 422 of stent 400 may all be of substantially the same size around the perimeter and along the length of stent 400 or cells 422 nearer inflow end 410 may be larger or smaller than the cells nearer outflow end 412.

A prosthetic heart valve incorporating stent 400 may include prosthetic valve leaflets, such as those described above in connection with the embodiment of FIGS. 3A-B. The prosthetic valve leaflets may be attached to stent 400 at a body or leaflet section 430, which may extend from outflow end 412 toward inflow end 410. Leaflet section 430 may have a substantially cylindrical shape as illustrated in FIG. 4A, but may take other shapes.

While leaflet section 430 is positioned closer to outflow end 412 of stent 400, an anchor or flange section 440 is positioned adjacent inflow section 410. Flange section 440 may be integral with the remainder of stent 400 and may be defined at least in part by a plurality of cells 422 and/or struts 420 extending radially outwardly. The stent 400, including flange section 440, may be formed by laser cutting a single tube of material into the desired shape, although other methods of manufacture may be suitable. The cells 422 and/or struts 420 defining flange section 440 may be configured to extend at an angle of about 90 degrees from a longitudinal axis L2 of stent 400 when stent 400 is in the relaxed or expanded condition. It should be understood that other angles or ranges of angles, for example between about 60 degrees and about 120 degrees, between about 70 degrees and about 110 degrees, or between about 80 degrees and about 100 degrees, may also be suitable. It should further be noted that flange section 440 need not be integral with the remainder of stent 400, and may be attached to leaflet section 430 and formed of materials other than Nitinol. Flange section 440 transitions to leaflet section 430 via a reduced diameter transition section, referred to herein as annulus groove 470. When in the relaxed or expanded condition, the diameter D1 of stent 400 at the innermost portion of annulus groove 470 is smaller than the diameter of the flange section 440 and the diameter D2 of leaflet section 430. Preferably, when implanted, the diameter D1 of annulus groove 470 at the innermost portion is equal to or smaller than the diameter of native valve annulus VA, while diameter D2 is preferably larger than the inner diameter of the native valve annulus. This arrangement may facilitate better securement of stent 400 in the native anatomy, including the annulus and portions of native leaflets.

Figure 4B:
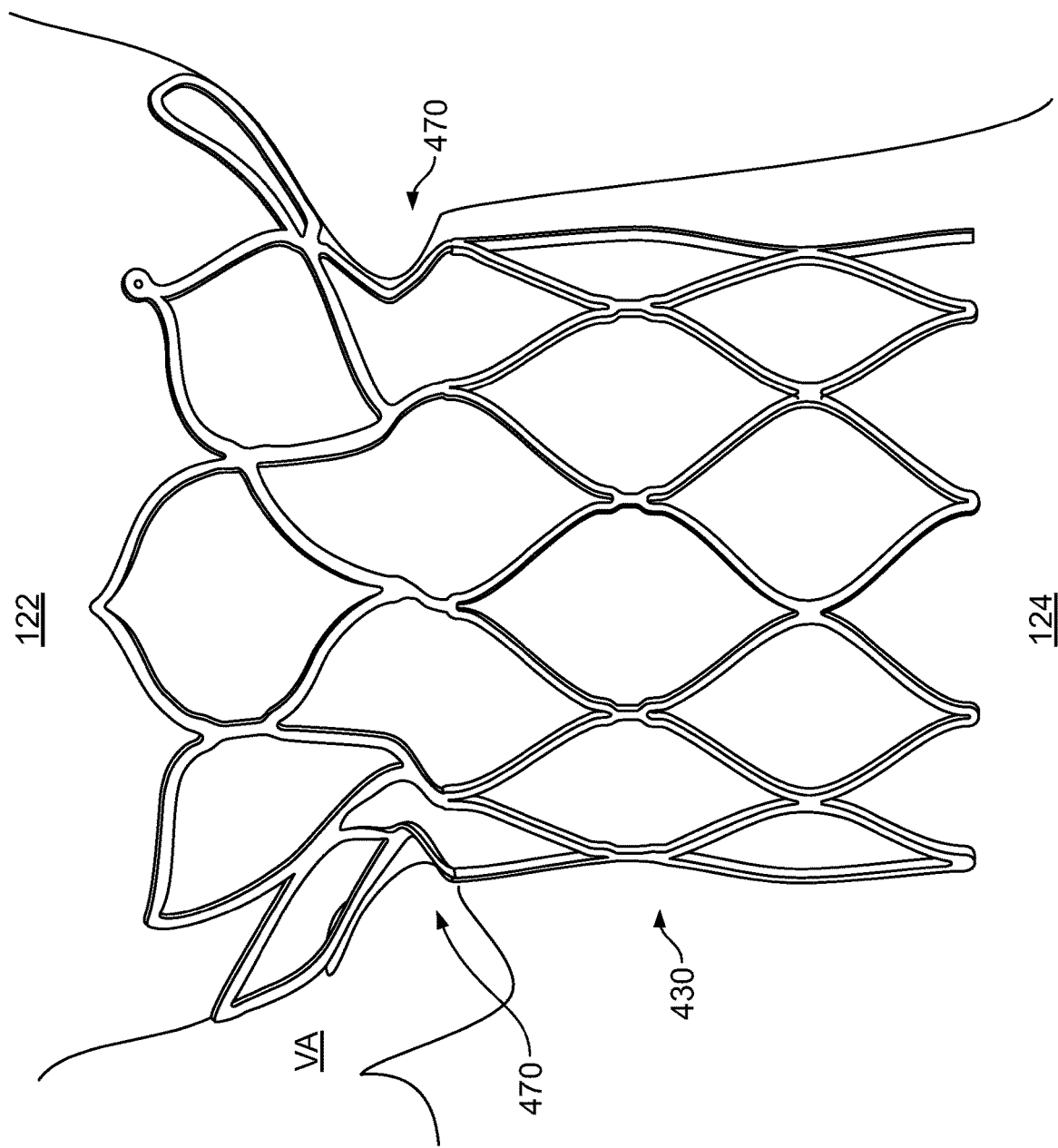
FIG. 4B is a schematic representation of the stent of FIG. 4A disposed in a native valve annulus.

In use, a prosthetic heart valve incorporating stent 400 may be positioned within a native valve annulus VA as illustrated in FIG. 4B, which omits from the illustration components of the prosthetic heart valve other than stent 400. When implanted, flange section 440 may be positioned in left atrium 122. The elastic properties of the struts forming flange section 440 and the above-described shape setting helps flange section 440 conform to the atrial surface of native valve annulus VA. During atrial systole when the prosthetic leaflets open, the forward force from left atrium 122 toward left ventricle 124 is relatively small and flange section 440 helps prevent the prosthetic heart valve incorporating stent 400 from slipping into left ventricle 124. Further, the innermost portion of annulus groove 470 is positioned adjacent native valve annulus VA, such that the sidewalls of annulus groove 470 perform a clamp-like function. During ventricular systole when the prosthetic leaflets close, the back pressure from left ventricle 124 toward left atrium 122 is relatively large. The annulus groove 470, in combination with the diameter D2 of leaflet section 430 being larger than the diameter of the native valve annulus VA, helps the valve resist slipping into left atrium 122.

As noted above, FIGS. 4A-B omit certain structures which may be used in addition to stent 400 to form a prosthetic heart valve. For example, one or more cuffs may be attached on flange section 430 and/or at annulus groove 470 to help prevent PV leak. The number of prosthetic leaflets within the leaflet section 430 may be one, two, three, or more. The cuffs and prosthetic leaflets may be formed of the same or similar materials as described above in connection with the embodiment of FIGS. 3A-B.

When being used in a prosthetic heart valve for replacing the native mitral valve of a patient, stent 400 is crimped to a collapsed condition and positioned within a catheter or similar structure of a delivery device prior to implantation. The method of delivering a prosthetic heart valve incorporating stent 400 may be substantially similar to that described in connection with stent 300 of FIGS. 3A-B. For example, if a transfemoral route of delivery is used, retaining tabs 460 on inflow end 410 of stent 400 may be connected to the delivery device to couple stent 400 to the delivery device until stent 400 is fully expanded. Retaining tabs (not illustrated) may be formed on outflow end 412 of stent 400, on the other hand, for retaining stent 400 in a delivery device during a transapical delivery. Further, the valve 400 may be implanted such that leaflet section 430 is substantially or fully in a supraannular position.

Figure 4C:
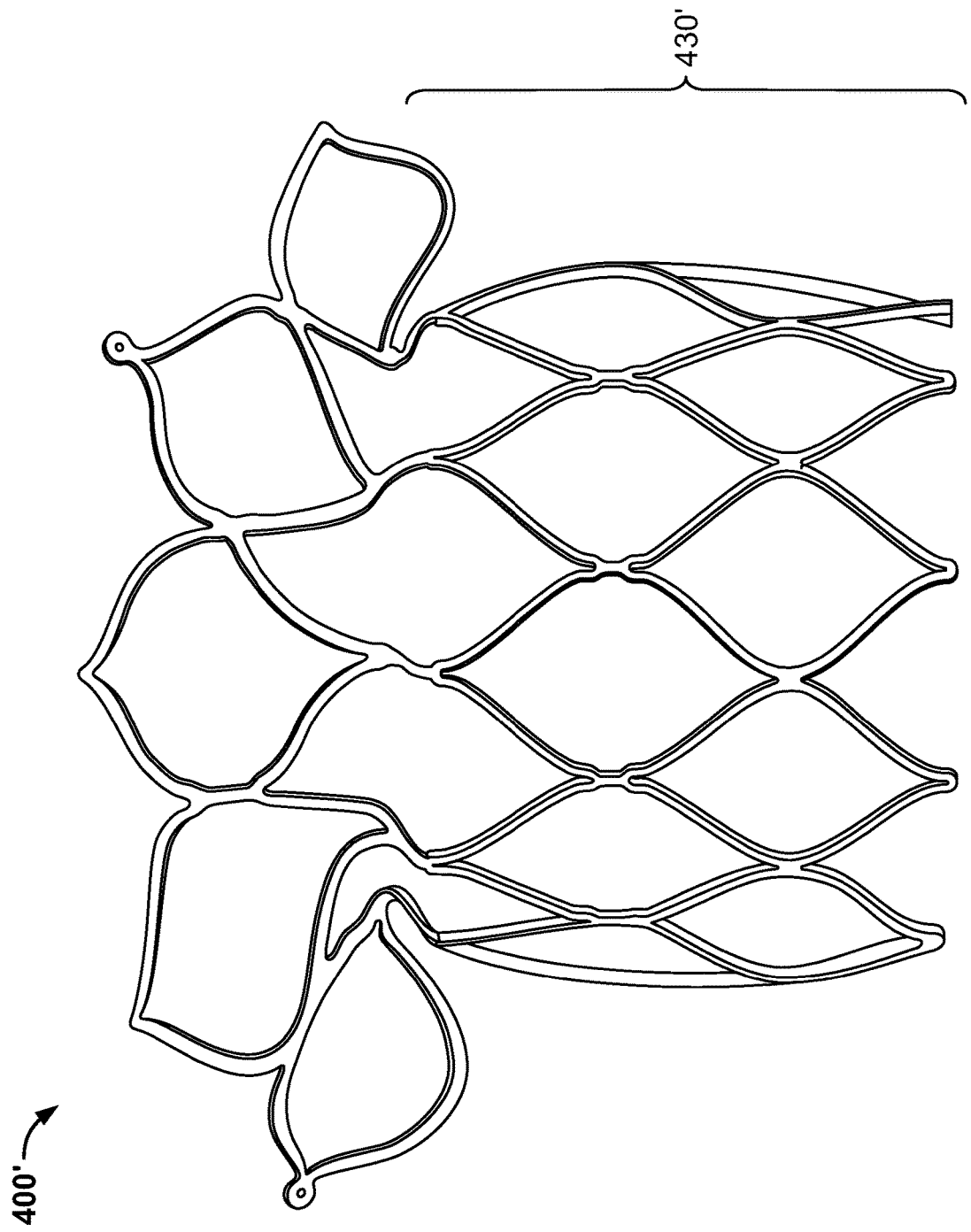
FIG. 4C is a front view of a front portion of a stent of a prosthetic heart valve according to a further embodiment of the disclosure.

As noted above, although leaflet section 430 is illustrated with a substantially cylindrical shape in FIG. 4A, other shapes are possible. For example, leaflet body 430' is illustrated in FIG. 4C as having a barrel shape. In other words, barrel-shaped leaflet section 430' has a circumference that is larger (i.e., projects farther radially outward) in a center portion than it is on either side of the center portion. The barrel-shaped body may reduce the interference of stent 400' with heart structures within a native ventricle. Further, as described above in connection with FIGS. 3A-B, leaflet section 430 may also be generally "D"-shaped to better conform to native annulus VA. For example, interference may be reduced in the sense that the relatively smooth barrel shape is less likely to "poke" or otherwise detrimentally engage with chordae tendinae or native leaflets.

Various modifications may be made to the embodiments disclosed herein without departing from the scope of the disclosure. For example, although stents and prosthetic heart valves are generally described for replacement of the mitral other bicuspid valves, variations may be made to these devices to replace tricuspid valves. Thus, the prosthetic valves may be provided with three leaflets, or more or fewer leaflets as desired. Similarly, although generally described as self-expanding prosthetic heart valves or stents, the principles described herein are also applicable to prosthetic valves that are not self-expanding, such as balloon-expandable prosthetic valves.

According to one embodiment of the disclosure, a stent has a collapsed condition and an expanded condition, the stent comprising a body having an outflow end and an inflow end; and an anchoring section adjacent the inflow end and including a first annular disc and a second annular disc, the first annular disc and the second annular disc each extending radially outwardly from the body when the stent is in the expanded condition; and/or the first disc has a smaller diameter than the second disc when the stent is in the expanded condition; and/or the second disc is positioned farther away from the outflow end than the first disc; and/or the first disc and the second disc are each formed of a braided material; and/or the braided material is Nitinol; and/or the anchoring section includes a gap between the first disc and the second disc when the stent is in the expanded condition; and/or the first disc is integral with the second disc; and/or the first disc and the second disc are each integral with the body; and/or there is substantially no overlap between the first disc and the body when the stent is in the collapsed condition; and/or the first disc flares away from the outflow end and the second disc flares toward the outflow end when the stent is in the expanded condition; and/or the first disc and the second disc each extend at an angle of about 90 degrees from a longitudinal axis of the body when the stent is in the expanded condition; and/or a prosthetic heart valve having at least two prosthetic heart valve leaflets positioned within the body.

According to another embodiment of the disclosure, a stent has a collapsed condition and an expanded condition, the stent comprising a body having a longitudinal axis, an outflow end, an inflow end, and a diameter in the expanded condition of the stent; an anchoring section adjacent the inflow end, and the anchoring section having a diameter in the expanded condition of the stent; and a transition section between the body and the anchoring section, the transition section in the expanded condition of the stent having a diameter that is smaller than the diameter of the body and smaller than the diameter of the anchoring section, wherein the anchoring section extends radially outwardly from the longitudinal axis of the body when the stent is in the expanded condition; and/or the anchoring section includes a plurality of struts forming cells; and/or the anchoring section is integral with the body; and/or the anchoring section extends radially outwardly from the longitudinal axis of the body at an angle of between about 80 degrees and about 100 degrees when the stent is in the expanded condition; and/or the anchoring section extends radially outwardly from the longitudinal axis of the body at an angle of about 90 degrees when the stent is in the expanded condition; and/or the body is substantially cylindrical; and/or the body has a center portion between the inflow end and the outflow end, the center portion having a circumference that is larger than a circumference of the body on either side of the center portion when the stent is in the expanded condition; and/or a prosthetic heart valve having at least two prosthetic heart valve leaflets positioned within the body.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A stent having a collapsed condition and an expanded condition, the stent comprising:
    a body having a longitudinal axis, an outflow end, an inflow end, and a diameter in the expanded condition of the stent;
    an anchoring section adjacent the inflow end, the anchoring section having a diameter in the expanded condition of the stent; and
    a transition section between the body and the anchoring section, the transition section in the expanded condition of the stent having a diameter that is smaller than the diameter of the body and smaller than the diameter of the anchoring section,
    wherein the anchoring section extends radially outwardly from the longitudinal axis of the body at a first angle of between about 80 degrees and about 100 degrees when the stent is in the expanded condition, and
    wherein, when the stent is deployed, the anchoring section extends radially outwardly from the longitudinal axis of the body at a second angle smaller than the first angle.

2. The stent of claim 1, wherein the anchoring section includes a plurality of struts forming cells.

3. The stent of claim 1, wherein the anchoring section is integral with the body.

4. The stent of claim 1, wherein the anchoring section extends radially outwardly from the longitudinal axis of the body at an angle of about 90 degrees when the stent is in the expanded condition.

5. The stent of claim 1, wherein the body is substantially cylindrical.

6. The stent of claim 1, wherein the body has a center portion between the inflow end and the outflow end, the center portion having a circumference that is larger than a circumference of the body on either side of the center portion when the stent is in the expanded condition.

7. A prosthetic heart valve comprising:
a stent having:
  a body having a longitudinal axis, an outflow end, an inflow end, and a diameter in the expanded condition of the stent;
  an anchoring section adjacent the inflow end, the anchoring section having a diameter in the expanded condition of the stent;
  a transition section between the body and the anchoring section, the transition section in the expanded condition of the stent having a diameter that is smaller than the diameter of the body and smaller than the diameter of the anchoring section; and
  wherein the anchoring section extends radially outwardly from the longitudinal axis of the body at a first angle of between about 80 degrees and about 100 degrees when the stent is in the expanded condition, and
at least two prosthetic heart valve leaflets positioned within the body, and
wherein, when the stent is deployed, the anchoring section extends radially outwardly from the longitudinal axis of the body at a second angle smaller than the first angle.

8. The prosthetic heart valve of claim 7, wherein the at least two prosthetic heart valve leaflets are configured to be in a supraannular position with respect to a native valve annulus when implanted.

9. The prosthetic heart valve of claim 7, wherein the anchoring section includes a plurality of struts forming cells.

10. The prosthetic heart valve of claim 7, wherein the anchoring section is integral with the body.

11. The prosthetic heart valve of claim 7, wherein the anchoring section extends radially outwardly from the longitudinal axis of the body at an angle of about 90 degrees when the stent is in the expanded condition.

12. The prosthetic heart valve of claim 7, wherein the body is substantially cylindrical.

13. The prosthetic heart valve of claim 7, wherein the body has a center portion between the inflow end and the outflow end, the center portion having a circumference that is larger than a circumference of the body on either side of the center portion when the stent is in the expanded condition.

* * * * *